United States Patent [19]

Banerjee

[11] Patent Number: 4,975,378

[45] Date of Patent: Dec. 4, 1990

[54] METHOD FOR ISOTOPE DILUTION CHROMATOGRAPHY

[76] Inventor: Sujit Banerjee, 1832 Jacksons Creek Point, Marietta, Ga. 30068

[21] Appl. No.: 226,075

[22] Filed: Jul. 26, 1988

[51] Int. Cl.$^5$ .................... G01N 23/00; G01N 23/06; G01N 30/02; B01D 15/03
[52] U.S. Cl. ...................................... 436/57; 436/161; 422/70; 422/71; 210/635; 210/656
[58] Field of Search ................... 436/57, 161; 422/70, 422/71; 435/803; 210/635, 656

[56] References Cited

U.S. PATENT DOCUMENTS

| | | | |
|---|---|---|---|
| 3,666,854 | 5/1972 | Eisentraut | 436/808 |
| 3,768,979 | 10/1973 | Mead et al. | 422/71 |
| 3,929,410 | 12/1975 | Schloss | 436/57 |
| 4,734,377 | 3/1988 | Banerjee | 436/161 |

OTHER PUBLICATIONS

Cortes et al., Journal of Chromatography, 295 (1984), pp. 269–275.
Parkin, Journal of Chromatography, 303 (1984), pp. 436–439.
Banerjee, Analytical Chemistry, vol. 57, No. 13, Nov. 1985, pp. 2590–2592.
Banerjee et al., Journal of Chromatography, 396 (1987), pp. 169–175.
Banerjee, Analytical Chemistry, vol. 60, No. 13, Aug. 1988, pp. 1626–1629.

*Primary Examiner*—Robert J. Warden
*Assistant Examiner*—Thalia P. Vassilatos

[57] ABSTRACT

Method for integrating isotope dilution analysis with chromatography. One embodiment of the invention includes a liquid chromatographic column, a radiochemical detector, an eluent that contains an additive at saturation and a radiochemically labeled derivative of the analyte to be determined. When the analyte, which is not radioactive, is injected, its movement through the column occurs more slowly than the movement of the radioactive derivative situated on the column outside the analyte band. As a result, radioactivity enters the analyte band and isotope dilution occurs. The distribution of radioactivity within the band is used to determine the amount of analyte injected.

3 Claims, 5 Drawing Sheets

METHOD FOR ISOTOPE DILUTION CHROMATOGRAPHY

BACKGROUND OF THE INVENTION

This invention relates generally to isotope dilution analysis and to chromatography, and has particular reference to a novel method for practicing isotope dilution analysis with the apparatus of chromatography.

In prior art isotope dilution analysis, an unknown quantity of analyte is determined through an isotopically labeled derivative of the analyte. In one embodiment of the art said derivative is radioactive. A known quantity of the radioisotope of known specific activity is added to the sample matrix, and a known quantity of the analyte-radioisotope mixture is isolated therefrom. The specific activity of the added radioisotope is decreased through dilution with the analyte, and the decrease is proportional to the quantity of analyte present. The specific activity determination requires a knowledge of the amount of radioactivity in the isolated material, and also a knowledge of the total mass of compound that contains the activity. Mass measurements are difficult to make in trace work, and isotope dilution analysis is not, therefore, generally applicable to trace analysis. To some extent the difficulty can be overcome by methods such as sub-stoichiometric analysis, but these methods need to be developed on a case-by-case basis.

In chromatography, an analyte mixture is injected into a fluid that flows through a column. The components of the mixture are separated on the column and the outflow from the column is monitored by a suitable detector. The analyte of interest is sensed as it elutes from the column.

The applicant is not aware of any prior art that has addressed itself to the practice of isotope dilution analysis through the apparatus of chromatography by exploiting differences in retention between analyte and isotope. The closest prior art known to the applicant is U.S. Pat. No. 3,929,410 issued to Schloss. This patent is directed to a method of indirect analysis where a saturated solution containing a known amount of radioactive standard is allowed to equilibrate with an unknown amount of the same compound in its unlabelled form, and quantitation of the unlabelled material is made on the basis of the amount of radioactive standard remaining in the saturated solution. The present invention differs from the Schloss patent in that it utilizes the apparatus of chromatography to effect the dilution of isotope. Also, temperature changes are not required in the present invention, and it is not necessary to precisely saturate a known amount of a liquid phase with a known amount of the radioactive standard.

Another related prior art method has been disclosed by Banerjee in U.S. Pat. No. 4,734,377. This patent utilizes a liquid chromatographic system with the eluent saturated with an indicator. The indicator solubilizes or displaces the analyte from the stationary phase. Analytes that cannot be detected directly can be indirectly visualized through the indicator. The present invention differs from the Banerjee patent in that detection is based on the isotope dilution principle, in that the indicator and analyte are chromatographically identical, and in that the analyte is selectively detected. Other prior art developed in the course of a preliminary search consists of Cortes and Stevens (J. Chromatogr. 295(1984)269-275), Parkin (J. Chromatogr. 303(1984)436-439), Banerjee (Anal. Chem. 57(1985) 2590-2592), Banerjee and Castrogivanni (J. Chromatogr. 396(1987) 169-175), Banerjee (Anal. Chem. 60(1988)1626-1629), and U.S. Pat. Nos. 3,666,854 and 3,768,979.

SUMMARY OF THE INVENTION

The present invention has as its principal objective the provision of a method for indirectly detecting and quantitating analytes through a combination of chromatography and isotope dilution analysis. Stated another way, the invention provides a means through which isotope dilution analysis can be used as a mechanism of indirect detection in chromatography. The apparatus of the invention in one embodiment thereof is essentially comprised of a chromatographic column through which a sample can be passed, an eluent that contains a mixture of an additive and an isotopically labeled derivative of the analyte to be determined, and a detector tuned to respond to said derivative. The eluent is passed through the column until the stationary phase of the column is equilibrated with the mixture of additive and said derivative. When the analyte to be determined is injected, the movement of the analyte through the column occurs more slowly than the movement through the column of said derivative situated on the column immediately behind the analyte band. As a result, said isotopic derivative enters the analyte band and isotope dilution occurs within said band. The extent of dilution and the distribution of isotope within said band can be used to measure the amount of analyte injected onto the column.

DESCRIPTION OF THE PREFERRED EMBODIMENTS

Figure 1:
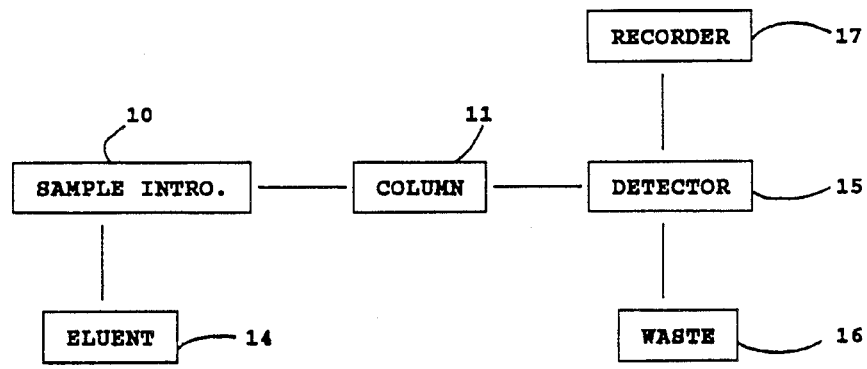
FIG. 1 is a diagrammatic illustration in the form of a flow chart of a prior art chromatographic apparatus.

Reference is now made to the drawings, and in particular to FIG. 1 illustrating prior art chromatographic apparatus. In FIG. 1, the sample which may contain a mixture of analytes is introduced into an eluent stream as indicated at 10, which flows into a chromatographic column 11. The eluent is contained in reservoir 14. The column 11 can be any one of a number of types whose construction is well known in the art. The outflow from the column passes through a known type of detector 15, as for example a radiochemical detector, and from thence to waste as indicated by 16. The output from the detector is recorded by a recording device 17 of a known type.

In the method embodying the invention, a structurally similar analog (An*) of the analyte (An) to be determined is added to the eluent. For example, said analog could be an isotopically labeled derivative of An. It is necessary for An* to be chromatographically identical to An. That is to say An and An* should both have the same retention time when they are subjected to the same conditions. The detector is selected to respond to An*. If An* is radioactive, then the detector is such that it detects the radioactivity of An*.

Figure 2:
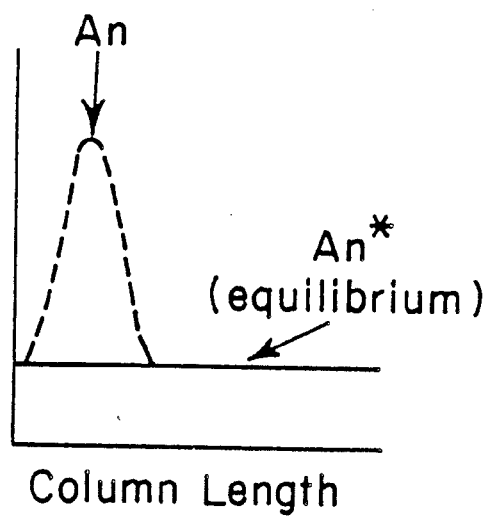
FIG. 2 is a diagrammatic illustration of the initial distribution of an analyte (An) upon injection on a column containing An*, an isotope of An.

The eluent is pumped through the column, and at equilibrium, An* is evenly distributed through the stationary phase. Referring now to FIG. 2, the bold line represents the presence of An* at equilibrium on the stationary phase. When the analyte to be determined is injected it is superimposed over the An* layer. The analyte is represented by the dashed curve in FIG. 2. The relative proportion of An* has been exaggerated in FIG. 2 for the sake of clarity.

Figure 3:
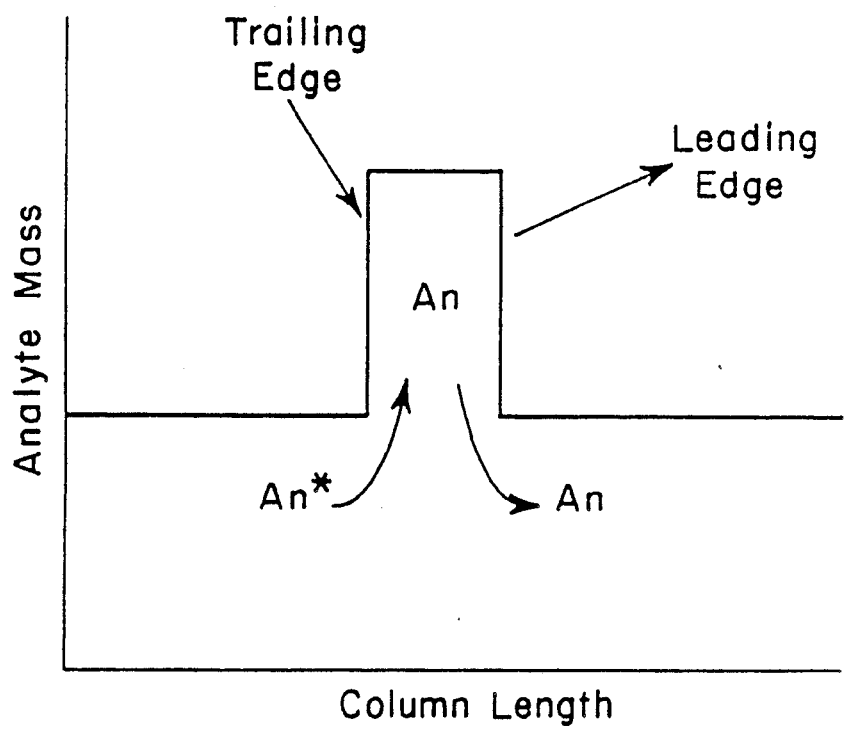
FIG. 3 is a diagrammatic illustration of the mechanism through which an injected band of An is enriched with its isotope An*.

A requirement for the successful practice of the invention is that the retention of An (or An*) increase with increasing mass of An. To aid in the understanding of what the invention does, reference is made to FIG. 3. If the concentration of injected An on the stationary phase is much greater than the concentration of An* already present, the An band is retained longer than the An* present on either side of it. As a result, the An* immediately following the band continuously moves into the trailing edge of the band as shown in FIG. 3. This An* equilibrates with the An in the band, and isotope dilution occurs. Now, since the mass of An greatly exceeds the mass of An* within the band, the material leaving the band from its leading edge contains more An than An* As a result, the band is progressively enriched in An*, that is the An is "washed" out.

The above situation only applies to a very narrow band whose isotopic distribution is homogenous. It is assumed that when the incoming An* is diluted with material in the band, the isotopic composition within the band changes evenly. In practice, most bands are too wide to be homogeneously diluted. Thus, the trailing edge of the band where the An* enters will be enriched in An*, and the leading edge where the An exits will be correspondingly depleted of isotope.

Figure 4:
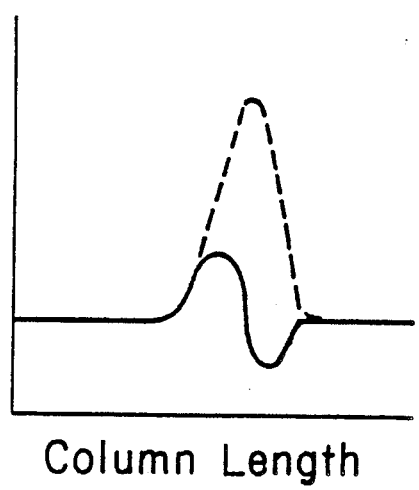
FIG. 4 is a diagrammatic illustration of the distribution of an analyte (An) and its isotope An* after partial movement of An through a column containing An*.

Reference is now made to FIG. 4 where the injected band depicted by the dashed curve has progressed through the column, and isotopic enrichment-depletion as described above has occurred within the band. The bold curve depicts the distribution of An* within the band. When the leading edge of the band which is depleted of An* enters the detector, it induces a negative signal which swings positive as the trailing edge of the band which is enriched in An* moves through.

One means of meeting the key requirement that retention of An increase with increasing An mass is to saturate the eluent with a suitable additive (Add). The additive is chosen to be chromatographically similar to An but not identical to it. Under these conditions, Add and An are expected to compete for similar sites on the column.

An approximate mathematical representation of the retention of An in the presence of Add was derived by S. Banerjee (Anal. Chem. August 1988). Since the eluent contains An* and is also saturated with Add, it follows that at equilibrium, the stationary phase will be coated with the Add-An* mixture. The Add-An* coating can be considered as a homogenous liquid layer influenced by the potential field of the stationary phase. Since An and An* are assumed to be chromatographically indistinguishable, they can be collectively defined as A; that is A=An+An* The capacity factor of A is $$k_A' = n_A^{sp}/n_A^{el} \quad (1)$$

where $n_A^{sp}$ and $n_A^{el}$ and are the number of moles of A in the stationary phase and in the eluent respectively. The mole fraction of A in the organic layer coating the stationary phase is $$x_A^{sp} = \frac{n_A^{sp}}{n_A^{sp} + n_{Add}^{sp}} \quad (2)$$

The molar solubility of A in the eluent, $s_A^{el}$, is given by $$s_A^{el} = S_A^{el} x_A^{sp} \gamma_A^{sp} \quad (3)$$

where $S_A^{el}$ is the solubility of pure A, that is in the absence of any additive, and $\gamma_A^{sp}$ is the activity coefficient of A in the stationary phase coating. The number of moles of A in volume V of eluent is $$n_A^{el} = s_A^{el} V \quad (4)$$

Suitable substitution of terms from equation 2-equation 4 into equation 1 gives $$k_A' = \frac{n_A^{sp} + n_{Add}^{sp}}{\gamma_A^{sp} S_A^{el} V} \quad (5)$$

Both $(n_A^{sp} + n_{Add}^{sp})$ and $\gamma_A^{sp}$ will be sensitive to An mass, with $\gamma_A^{sp}$ being the more affected. Most hydrophobic compounds show positive deviations from Raoult's law, and $\gamma_A^{sp}$ will decrease as analyte mass increases. Accordingly, k' will increase with $x_A^{sp}$, that is with analyte mass.

The method of the invention has been applied with the apparatus of high performance liquid chromatography to the detection of benzene, with the use of a Varian 5560 pump, a 2×30 mm Brownlee μC18 column, a Radiomatic FLO-ONE radioactivity monitor with heterogeneous detection, and a Hewlett Packard 3390A recorder, which were assembled as shown in FIG. 1. The eluent was prepared by stirring a solution of 10 volume percent methanol in water with toluene for about 12 hours, and allowing the two phases to separate. The methanol-water phase was spiked with [$^{14}$C]benzene. The final activity in the eluent was about 60 cpm/μL. The eluent was then pumped through the system until the detector baseline stabilized.

Figure 5:
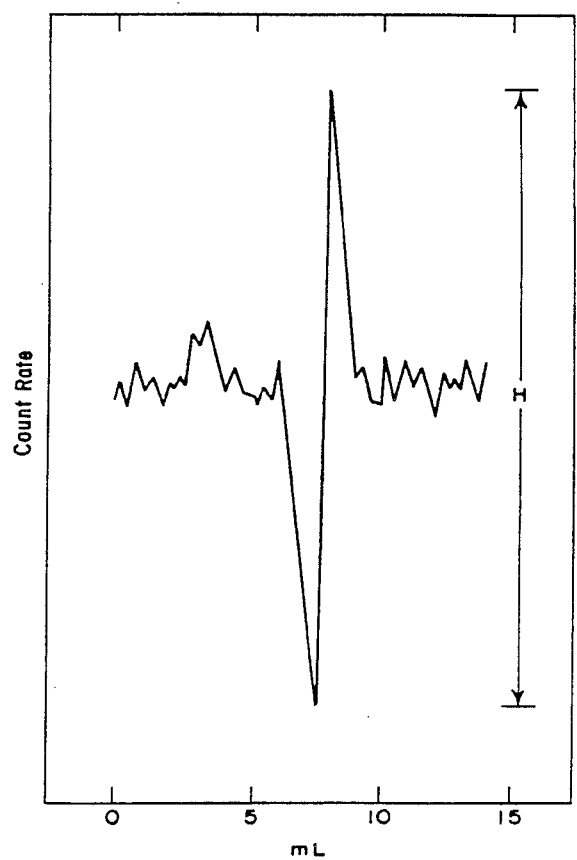
FIG. 5 is a chromatogram produced by the method of the invention.

A solution of benzene (49 μg) in 50 volume percent methanol in water was injected, and the chromatogram shown in FIG. 5 was obtained. The relationship between peak-to-trough height (H) and the amount of benzene injected is shown by the data in the first two columns of Table 1. The third column in Table 1 confirms that the retention of benzene increases as the amount of benzene injected increases in accord with equation 5. Hence, if a sample containing benzene at an unknown concentration was injected, the amount of benzene contained in the sample could be determined by

TABLE 1

| | Isotope Dilution Chromatographic Analysis of Benzene | |
|---|---|---|
| μg injected | response H (arbitrary units) | retention time (min) |
| 9.6 | 22.5 | 7.94 |
| 20 | 42 | 8.12 |
| 49 | 76 | 8.30 | measuring H for the sample, and calculating the desired concentration from a calibration curve.

The peak-to-trough height (H) should increase as the activity of An in the eluent increases, since the degree of enrichment of the analyte band would also correspondingly increase. This relationship was verified under conditions where the above-mentioned eluent was spiked with varying levels of [$^{14}$C] benzene activity, and an injection of benzene (48 μg) was made at each level. The data are provided in Table 2, and they clearly demonstrate that sensitivity improves with increasing eluent activity.

The method is extremely selective, since the isotopic derivative in the eluent can only be diluted with a species that is chromatographically identical to it. In one example, a solution of unleaded gasoline was spiked with benzene, dissolved

TABLE 2

| Dependence of response (H) on eluent radioactivity | |
|---|---|
| activity in eluent (arbitrary units) | response H (arbitrary units) |
| 2 | 16 |
| 4 | 30 |
| 6 | 46 |
| 8 | 64 |
| 10 | 78 | in 50 volume percent methanol in water, and injected into the chromatographic system used to develop the trace in FIG. 5. Except for a weak signal at the void volume corresponding to the injection solvent, the only signal observed was that of benzene. Similarly, a solution of m-xylene spiked with benzene and injected under the same chromatographic conditions used to obtain FIG. 5 gave rise to only the benzene signal.

Saturation of the eluent with the additive leads to optimum response, but it is not an absolute requirement for the successful practice of the invention. The additive enables the retention of An to increase with increasing An mass. When the additive is present at less than saturation, the dependence of An retention on An mass is reduced. A blank consisting of 50 volume percent methanol in water and a solution containing 54 μg of benzene in 50 volume percent methanol in water were each spiked with [$^{14}$C]benzene and injected separately into an eluent of 10 volume percent methanol in water containing only toluene. The toluene content in the eluent was varied between 0 to 100 of saturation, and the injections were repeated after each adjustment. A comparison of the retention of the radioactive material injected in the blank, and in the solution containing benzene as a function of the percentage of toluene saturation is provided in Table 3. It is evident that the difference in retention ($\Delta V_R$) increases as the toluene level is raised in the eluent.

From the foregoing description it will be evident that the invention provides a novel and very advantageous method for the indirect detection of analytes. A novel feature of the invention is that isotope dilution occurs continuously on the column. Another novel feature is that the method allows very high chromatographic selectivity, since isotope dilution only occurs

TABLE 3

Dependence of the Retention Volume $V_R$ of [$^{14}$C]Benzene on Toluene Content in the Eluent and on the Mass of Injected Benzene

| toluene (percent of saturation) | $V_R$ (mL) | | $\Delta V_R$ (mL) |
| | blank + [$^{14}$C]benzene | benzene (54 μg) + [$^{14}$C]benzene | |
|---|---|---|---|
| 0 | 3.38 ± 0.01 | 3.43 ± 0.01 | 0.05 |
| 20 | 3.63 ± 0.01 | 3.73 ± 0.03 | 0.10 |
| 40 | 4.40 ± 0.01 | 4.50 ± 0.02 | 0.10 |
| 60 | 6.00 ± 0.06 | 6.10 ± 0.01 | 0.10 |
| 80 | 8.63 ± 0.02 | 8.88 ± 0.05 | 0.25 |
| 100 | 7.24 ± 0.05 | 7.59 ± 0 | 0.35 | with the analyte of interest. This feature is exceptionally useful since it greatly minimizes interferences. Yet another important feature is that very high sensitivity can be potentially achieved, since a nonradioactive analyte can be determined with the sensitivity approximating that of radiochemical analysis. As will be understood by those familiar with the art, the invention may be embodied in other specific forms without departing from the spirit or essential characteristics thereof.

I claim:

1. A method of detecting an analyte in a sample using chromatography and isotope dilution comprising:
    (a) providing a chromatography system having a chromatographic column, a stationary phase within said column, and an eluent containing an analog of the analyte to be detected and an additive;
    (b) contacting the eluent with the stationary phase of the column until the stationary phase is equilibrated with the analog in the eluent;
    (c) adding the sample to the stationary phase of the column to form a sample band and passing the sample band through the stationary phase of the column with the eluent whereby movement of any analyte in the sample band through the stationary phase of the column occurs at a different rate than movement of the analog in the eluent that is adjacent to the sample band so that any analyte in the sample causes the sample band to be progressively enriched with said analog as said sample band moves through the stationary phase of the column, and wherein the additive is such that it induces the difference between the rate of movement of the analyte band and that of the analog material by enabling the rate of movement of the analyte to be dependent upon the mass of analyte injected; and
    (d) detecting a distribution profile of the analog in the sample band as the sample band emerges from the column and detecting and quantitating and analyte in the sample from the distribution profile.

2. A method as defined in claim 1 wherein the analog is an isotopically labeled derivative of the analyte.

3. A method as defined in claim 1 wherein the analog is a radioactive derivative of the analyte.

* * * * *